United States Patent [19]

Hsiao et al.

[11] Patent Number: 5,253,171
[45] Date of Patent: Oct. 12, 1993

[54] PARALLEL PROCESSING METHOD AND APPARATUS BASED ON THE ALGEBRA RECONSTRUCTION TECHNIQUE FOR RECONSTRUCTING A THREE-DIMENSIONAL COMPUTERIZED TOMOGRAPHY (CT) IMAGE FROM CONE BEAM PROJECTION DATA

[75] Inventors: Meng-Ling Hsiao; Wayne J. Eberhard, both of Schenectady, N.Y.; Yves L. Trousset, Palaiseau, France

[73] Assignee: General Electric Company, Schenectady, N.Y.

[21] Appl. No.: 586,163
[22] Filed: Sep. 21, 1990
[51] Int. Cl.$^5$ .................. G06F 15/00; A61B 6/00
[52] U.S. Cl. .................. 364/413.19; 378/4; 378/10
[58] Field of Search .......... 364/413.14, 413.19, 364/413.26; 378/4, 10

[56] References Cited

U.S. PATENT DOCUMENTS 5,023,895 6/1991 McCroskey et al. .............. 378/4

OTHER PUBLICATIONS

"Convolutional Reconstruction from Cone-Beam Projection Data", G. N. Minerbo, IEEE Trans. Nucl. Sci., vol. NS-26, No .2, pp. 2682–2684 (Apr. 1979).
"An Inversion Formula for Cone-Beam Reconstruction", SIAM J. Math., vol. 43, No. 3, pp. 546–552 (Jun. 1983).
"Practical Cone-Beam Algorithm", L. A. Feldlamp et al., J. Opt. Soc. Am. A., vol. 1, No. 6, pp. 612–619 (Jun. 1984).
"Image Reconstruction from Cone-Beam Projections: Necessary and Sufficient Conditions and Reconstruction Methods", B. D. Smith, IEEE Trans. Med. Imag., vol. MI-44, pp. 14–25 (Mar. 1985).
"Quantitative Cone-Beam Construction", H. Hu, et al., SPIE Medical Imaging III: Image Processing, vol. 1092, pp. 492–501 (1989).
"Algebraic Reconstruction Techniques (ART) for TYhree-dimensional Electron Microscopy and X-ray Photography", R. Gordon, et al., J. Theor. Biol., 29, pp. 471–481 (1970).
"ART: Mathematics and Applications-A Report on the Mathematical Foundations and on the Applicability to Real Data of the Algebraic Reconstruction Techniques", G. T. Herman, J. Theor. Biol., 43, pp. 1–32 (1973).
"Iterative Three-Dimensional Reconstruction from Twin-Cone Beam Projections", M. Schlindwein, IEEE Trans. Nucl. Sci., vol. NS-25, No. 5, p. 1135–1143 (Oct. 1978).
"Comparison of 3-D Tomographic Algorithms for Vascular Reconstruction", A. Rougea et al., SPIE vol. 914 Medical Imaging II, p. 397–405 (1988).
"The Dynamic Spatial Reconstructor", R. A. Robb et al., J. Med. Syst., vol. 4, No, 2, pp. 253–288 (1980).

Primary Examiner—Roy N. Envall, Jr.
Assistant Examiner—Khai Tran
Attorney, Agent, or Firm—Paul Webb, II

[57] ABSTRACT

A parallel processing architecture and method, based on the 3D Algebra Reconstruction Technique (ART), for iteratively reconstructing from cone beam projection data a 3D voxel data set V representing an image of an object. The cone beam projection data is acquired by employing a cone beam x-ray source and a two-dimensional array detector to scan the object along a source scanning trajectory to obtain, at each of a plurality of discrete source positions $\theta_i$ on the source scanning trajectory, a 2D measured cone beam pixel data set $P_i$. The 3D voxel data set V is subdivided into or organized as a plurality m of independent voxel subcubes $V^0$ through $V^{m-1}$ each containing a plurality of voxels. As a result of the subdivision of the 3D voxel data set V into voxel subcubes, the 2D measured cone beam pixel data set $P_i$ (measured projection data array) is correspondingly subdivided for each source position $\theta_i$ into projection data subsets, with overlapping regions between one or more adjacent projection data subsets corresponding to adjacent voxel subcubes. Each voxel subcube and its corresponding projection data strip or subset is processed in parallel with other pairs of voxel subcubes and corresponding projection data strips or subsets, without interference. A bi-level parallel-processor architecture is employed for iterative reproject and merge, and split and backproject operations.

22 Claims, 7 Drawing Sheets

REPROJECTION IN PARALLEL

REPROJECT VOXEL SUBCUBE $V^0$ TO SUBSET $P_i^0$

REPROJECT VOXEL SUBCUBE $V^0$ TO SUBSET $P_i^1$

REPROJECT VOXEL SUBCUBE $V^0$ TO SUBSET $P_i^2$

⋮

REPROJECT VOXEL SUBCUBE $V^{m-1}$ TO SUBSET $P_i^{m-1}$

MERGE

$$P_i = P_i^0 + P_i^1 + P_i^2 + \cdots + P_i^{m-1}$$

FIG. 7

SPLIT

SPLIT CORRECTION DATA SET $E_i$ INTO SUBSETS $E_i^0, E_i^1, E_i^2, \ldots, E_i^{m-1}$ ACCORDING TO GEOMETRY

BACKPROJECT IN PARALLEL

USE $E_i^0$ TO CORRECT VOXEL SUBCUBE $V^0$

USE $E_i^1$ TO CORRECT VOXEL SUBCUBE $V^1$

USE $E_i^2$ TO CORRECT VOXEL SUBCUBE $V^2$

⋮

USE $E_i^{m-1}$ TO CORRECT VOXEL SUBCUBE $V^{m-1}$

PARALLEL PROCESSING METHOD AND APPARATUS BASED ON THE ALGEBRA RECONSTRUCTION TECHNIQUE FOR RECONSTRUCTING A THREE-DIMENSIONAL COMPUTERIZED TOMOGRAPHY (CT) IMAGE FROM CONE BEAM PROJECTION DATA

BACKGROUND OF THE INVENTION

The present invention relates generally to three-dimensional (3D) computerized tomography (CT) and, more particularly, to methods and apparatus employing parallel processing for reconstructing a 3D image of an object from cone beam projection data.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a "stack of slices" approach is employed. Acquiring a 3D data set a 2D slice at a time is inherently tedious and time-consuming. Moreover, in medical applications, motion artifacts occur because adjacent slices are not imaged simultaneously. Also, dose utilization is less than optimal, because the distance between slices is typically less than the x-ray collimator aperture, resulting in double exposure to many parts of the body.

A more recent approach, based on what is called cone beam geometry, employs a two-dimensional array detector instead of a linear array detector, and a cone beam x-ray source instead of a fan beam x-ray source, for much faster data acquisition. To acquire cone beam projection data, an object is scanned, preferably over a 360° angular range, either by moving the x-ray source in a circular scanning trajectory, for example, around the object, while keeping the 2D array detector fixed with reference to the source, or by rotating the object while the source and detector remain stationary. In either case, it is relative movement between the source and object which effects scanning, compared to the conventional 2D "stack of slices" approach to achieve 3D imaging of both medical and industrial objects, with improved dose utilization.

However, image reconstruction becomes complicated and requires massive computational power when a 3D image is reconstructed from cone beam projection data, in contrast to reconstruction of a 2D image from fan beam projection data.

Literature discussing the cone beam geometry for 3D imaging and generally relevant to the subject matter of the invention includes the following: Gerald N. Minerbo, "Convolutional Reconstruction from Cone-Beam Projection Data", IEEE Trans. Nucl. Sci., Vol. NS-26, No. 2, pp. 2682-2684 (Apr. 1979); Heang K. Tuy, "An Inversion Formula for Cone-Beam Reconstruction", SIAM J. Math., Vol. 43, No. 3, pp. 546-552 (June 1983); L. A. Feldkamp, L. C. Davis, and J. W. Kress, "Practical Cone-Beam Algorithm", J. Opt. Soc. Am.A., Vol. 1, No. 6, pp. 612-619 (June 1984); Bruce D. Smith, "Image Reconstruction from Cone-Beam Projections: Necessary and Sufficient Conditions and Reconstruction Methods", IEEE Trans. Med. Imag., Vol. MI-44, pp. 14-25 (March 1985); and Hui Hu, Robert A. Kruger and Grant T. Gullberg, "Quantitative Cone-Beam Construction", SPIE Medical Imaging III: Image Processing, Vol. 1092, pp. 492-501 (1989). In general, this literature discloses various formulas for reconstruction of an image, including the use of a 3D Fourier transform or a 3D Radon transform. Questions of data completeness achieved with various source scanning trajectories are also considered.

The present invention is an implementation of the Algebra Reconstruction Technique (ART) for reconstructing an image of an object from its projections. The ART is an iterative algorithm which uses raysums to correct each voxel (volume element) of the reconstructed image at each iteration. The ART was initially disclosed in Richard Gordon, Robert Bender and Gabor T. Herman, "Algebraic Reconstruction Techniques (ART) for Three-dimensional Electron Microscopy and X-ray Photography", J. Theor. Biol., 29, pp. 471-481 (1970). Details regarding the mathematical foundations of the ART algorithm were described in Gabor T. Herman, Arnold Lent and Stuart W. Rowland, "ART: Mathematics and Applications—A Report on the Mathematical Foundations and on the Applicability to Real Data of the Algebraic Reconstruction Techniques", J. Theor. Biol., 43, pp. 1-32 (1973). Extension of the additive ART to 3D cone beam geometry is described in M. Schlindwein, "Iterative Three-Dimensional Reconstruction from Twin-Cone Beam Projections", IEEE Trans. Nucl. Sci., Vol. NS-25, No. 5, pp. 1135-1143 (October 1978). The ART was recently used for vascular reconstruction, as reported in A. Rougea, K. M. Hanson and D. Saint-Felix, "Comparison of 3-D Tomographic Algorithms for Vascular Reconstruction", SPIE, Vol. 914 Medical Imaging II, pp. 397-405 (1988).

In general, the Algebra Reconstruction Technique requires a large amount of computation time, and has not been implemented with parallel processing techniques.

In view of the parallel processing aspect of the present invention, the system described in Richard A. Robb, Arnold H. Lent, Barry K. Gilbert, and Aloysius Chu, "The Dynamic Spatial Reconstructor", J. Med. Syst., Vol. 4, No. 2, pp. 253-288 (1980) is relevant. The Dynamic Spatial Reconstructor employs twenty-eight x-ray sources and twenty-eight x-ray imaging systems in a synchronous scanning system to acquire data all at one time for a subsequent "stack of slices" reconstruction using conventional 2D reconstruction algorithms. The Robb et al. reference refers to the use of "high-speed parallel processing techniques" for the reconstruction computation.

SUMMARY OF THE INVENTION

Accordingly, it is an object of the invention to provide practical methods and apparatus for reconstructing 3D images from cone beam projection data, in view of the massive computational power required.

It is another object of the invention to provide methods and apparatus employing parallel processing for reconstructing 3D images from cone beam projection data.

It is another object of the invention to provide methods and apparatus which can reconstruct selected regions of interest, without spending processor time reconstructing regions outside the regions of interest.

Briefly, and in accordance with an overall aspect of the invention, a parallel processing architecture and method, based on the 3D Algebra Reconstruction Technique (ART), are defined for iteratively reconstructing from cone beam projection data a 3D voxel data set V representing an image of an object. The cone beam projection data is acquired by employing a cone beam x-ray source and a two-dimensional array detector to scan the object along a source scanning trajectory to obtain, at each of a plurality of discrete source positions $\theta_i$ on the source scanning trajectory, a 2D measured cone beam pixel data set $P_i$. The invention is applicable to reconstructing an object image from cone beam projection data acquired with any scanning geometry, so long as it is well defined. Examples include source scanning trajectories which comprise a single circle, dual or multiple parallel circles, dual perpendicular circles, or square waves on a cylindrical surface. However, in the embodiment described in detail hereinbelow, a circular source scanning trajectory lying in a plane perpendicular to a rotation axis passing through the object and perpendicular to all planes of the detector is employed. In this case, the discrete source positions $\theta_i$ are defined simply as angular positions. With various other scanning trajectories, the discrete source positions $\theta_i$ are defined by parameters in addition to or instead of angular position.

In accordance with the invention, the 3D voxel data set V is subdivided into or organized as a plurality of m of voxel subcubes $V^o$ through $V^{m-1}$ which are independent of each other. In other words, there is no overlap between adjacent voxel subcubes. Each voxel subcube contains a plurality of voxels. In the illustrated embodiment, boundaries between adjacent voxel subcubes lie in planes which are perpendicular to the detector planes and parallel to each other. However, independent voxel subcubes may be organized in a variety of ways.

As a result of the subdivision of the 3D voxel data set V into voxel subcubes, the 2D measured cone beam pixel data set $P_i$ (measured projection data array) is correspondingly subdivided for each source position $\theta_i$. In the embodiment described in detail herein wherein boundaries between adjacent voxel subcubes lie in parallel planes, the measured projection data array is divided into what may be termed projection data strips. In the more general case, the measured projection data array is divided into what may be termed projection data subsets.

Thus, for each source position $\theta_i$, each voxel subcube has a corresponding projection data strip or projection data subset. However, unlike the voxel subcubes, the projection data strips or subsets are not independent. In other words, dependent upon the particular scanning geometry defined and the particular voxel and pixel positions for each particular source position $\theta_i$, there are overlapping regions between one or more adjacent projection data strips or subsets corresponding to adjacent voxel subcubes.

Nevertheless, in accordance with the invention, each voxel subcube and its corresponding projection data strip or subset can be processed in parallel with other pairs of voxel subcubes and corresponding projection data strips or subsets, without interference. A bi-level parallel-processor architecture is employed. Backproject/reproject processor in level 0 selectively perform voxel driven backprojection from the projection data strips or subsets to the corresponding voxel subcubes, and voxel-driven reprojection from the voxel subcubes to the corresponding projection data strips or subsets. Each backproject/reproject processor operates on data which is independent of the data for the other backproject/reproject processors, so the processors can operate in parallel. At least one split/merge processor in level 1 splits a projection data set for a particular source position $\theta_i$, into projection data strips or subsets from reprojection into a projection data set. During iterative reconstruction implementing the Algebra Reconstruction Technique, for each source position $\theta_i$, data are sent back and forth between level 0 for backprojection and reprojection and level 1 for splitting and merging.

Preferably, level 1 is organized in a tree-type manner as a plurality of layers. The split/merge processors can comprise transputers.

More particularly, a method in accordance with the invention includes the steps of organizing the voxel data set V as a plurality m of independent voxel subcubes $V^o$ through $V^{m-1}$, each voxel subcube including a plurality of voxels; initializing the voxel data set V; and performing successive iterations to correct the values of at least selected voxels of the 3D voxel data set based on the measured cone beam data sets $P_i$. In a particular embodiment, boundaries between adjacent voxel subcubes lie in planes perpendicular to all planes of the 2D detector array and parallel to each other.

During each iteration, the values of at least the selected voxels for each of the discrete source positions $\theta_i$ on the source scanning trajectory are corrected by reprojecting each voxel subcube $V^o$ through $V^{m-1}$ to calculate pixel values for a corresponding 2D calculated projection data strip or subset from a group of calculated projection data strips or subsets $P_i^0$ through $P_i^{m-1}$ of a 2D calculated projection data set $P_i$ including a plurality of pixels, the projection data strips of subsets $P_i^0$ through $P_i^{m-1}$ overlapping in part; merging the calculated projection data strips of subsets $P_i^0$ through $P_i^{m-1}$ to calculate pixel values of the 2D calculated projection data set $P_i$, the step of merging including adding pixel values in any overlapping regions of the calculated projection data strips of subsets $P_i^0$ through $P_i^{m-1}$; calculating a 2D correction projection data set $E_i$ including a plurality of pixels by determining the normalized difference between the value of each pixel of the measured projection data set P and the value of the corresponding pixel of the calculated projection data set $P_i$ splitting the 2D correction projection data set $E_i$ into a plurality of 2D correction projection data strips or subsets $E_i^0$ through $E_i^{m-1}$ corresponding to the voxel subcubes $V^0$ through $V^{m-1}$, the 2D correction projection data strips or subsets sets $E_i^0$ through $E_i^{m-1}$ overlapping in part, including duplicating element values for any overlapping regions of the correction projection data strips or subsets $E_i^0$ through $E_i^{m-1}$; and backprojecting each correction projection data strip or subset $E_i^0$ through $E_i^{m-1}$ to correct voxel values in the corresponding voxel subcube of the plurality of voxel subcubes $V^0$ through $V^{m-1}$.

The step of merging is organized in a tree-type manner as a plurality of layers and includes, for each layer, merging groups of calculated projection data strips or subsets from the next lower layer to present a lesser number of calculated projection data subsets to the next higher layer, the lowest layer merging groups of the calculated projection data strips or subsets $P_i^0$ through $P_i^{m-1}$ from the step of reprojecting, and the highest layer producing the calculated projection data set $P_i$.

The step of splitting is also organized in a tree-type manner as a plurality of layers and includes, for each layer, splitting one or more correction projection data strips or subsets from the next higher layer to present a greater number of correction projection data strips or subsets to the next lower layer, the highest layer splitting the correction data set $E_i$, and the lowest layer producing the correction projection data strips or subsets $E_i^0$ through $E_i^{m-1}$.

The method further includes employing a plurality m of backproject/reproject processors corresponding to the voxel subcubes to perform the steps of reprojecting and backprojecting, and employing a plurality of split/merge processors connected in a tree structure to perform the steps of merging and splitting.

The method additionally includes, during each iteration, for each of the discrete source positions $\theta_i$, in conjunction with the steps of reprojecting each voxel subcube $V^0$ through $V^{m-1}$, calculating data values for a corresponding 2D normalizing factor data strip or subset from a group of 2D normalizing factor strips or subsets $N_i^0$ through $N_i^{m-1}$ of a 2D normalizing factor data set $N_i$ including a plurality of pixels, the 2D normalizing factor strips or subsets $N_i^0$ through $N_i^{m-1}$ overlapping in part; merging the normalizing factor data strips or subsets $N_i^0$ through $N_i^{m-1}$ to calculate element values of the 2D normalizing factor data set $N_i$; and, during the step of calculating the 2D correction data set $E_i$, employing the value of each corresponding element of the normalizing factor data set $N_i$.

The step of reprojecting is voxel driven and includes, for each voxel subcube of the plurality of voxel subcubes $V^0$ through $V^{m-1}$, initializing the corresponding calculated projection data strip or subset from the group of projection data subsets $P_i^0$ through $P_i^{m-1}$; initializing the corresponding normalizing factor data strip or subset from the group of normalizing factor data strips or subsets $N_i^0$ through $N_i^{m-1}$; and for each of the selected voxels of the 3D voxel data set V included in the particular voxel subcube, adding to the value of each pixel of the corresponding calculated projection data strip or subset from the group of calculated projection data strips or subsets $P_i^0$ through $P_i^{m-1}$ influenced by the selected voxel the voxel value multiplied by a weighting factor $h(p,v)$ determined for the voxel and pixel positions based on geometry such that pixel values are cumulated in the corresponding artificial projection data subset, and adding to the value of each element of the corresponding normalizing factor data strip or subset from the group of normalizing factor data strips or subsets $N_i^0$ through $N_i^{m-1}$ the square of the weighting factor $h(p,v)$ determined for the voxel and pixel positions based on geometry such that element values are cumulated in the corresponding normalizing factor data strip or subset.

The step of backprojecting is also voxel driven and includes, for each voxel subcube of the plurality of voxel subcubes $V^0$ through $V^{m-1}$, for each of the selected voxels of the 3D voxel data set V included in the particular voxel subcube, adding to the voxel value the value of each element of the corresponding 2D correction projection data strip or subset of the group of correction projection data strips or subsets $E_i^0$ through $E_i^{m-1}$ in a pixel position influenced by the selected voxel multiplied by a weighting factor $h(p,v)$ determined for the voxel and pixel positions based on geometry such that corrected voxel values are cumulated.

Parallel processing apparatus implementing the Algebra Reconstruction Technique in accordance with the invention includes a data memory for storing the voxel data set V organized as a plurality m of independent voxel subcubes $V^0$ through $V^{m-1}$, each voxel subcube including a plurality of voxels; and processing elements for initializing the voxel data set V and performing successive iterations to correct the values of at least selected voxels of the 3D voxel data set based on the measured cone beam data sets $P_i$, during each iteration correcting the values of at least the selected voxels for each of the discrete source positions $\theta_i$ on the source scanning trajectory.

The processing elements include in a level 0 a plurality m of backproject/reprojectors corresponding to the voxel subcubes, and in a level 1 at least one split/merge processor. The backproject/reproject processors are operable to reproject each voxel subcube $V^0$ through $V^{m-1}$ to calculate pixel values for a corresponding 2D calculated projection data subset from a group of calculated projection data subsets $P_i^0$ through $P_i^{m-1}$ of a 2D calculated projection data set $P_i$ including a plurality of pixels, the projection data subsets $P_i^0$ through $P_i^{m-1}$ overlapping in part. The split/merge processor is operable to merge the calculated projection data subsets $P_i^0$ through $P_i^{m-1}$ to calculate pixel values of the 2D calculated projection data set $P_i$, adding pixel values in any overlapping regions of the calculated projection data subsets $P_i^0$ through $P_i^{m-1}$. The processing elements include means for calculating a 2D correction projection data set $E_i$ including a plurality of pixels determining the normalized difference between the value of each pixel of the measured projection data set pixel $P_i$ and the value of the corresponding pixel of the calculated projection data set $P_i$. The split/merge processor is also operable to split the 2D correction projection data set $E_i$ into a plurality of 2D correction projection data subsets $E_i^0$ through $E_i^{m-1}$ corresponding to the voxel subcubes $V^0$ through $V^{m-1}$, duplicating element values for any overlapping regions of the correction projection data subsets $E_i^0$ through $E_i^{m-1}$. The backproject/reproject processors are also operable to backproject each correction projection data subset $E_i^0$ through $E_i^{m-1}$ to correct voxel values in the corresponding voxel subcube of the plurality of voxel subcubes $V^0$ through $V^{m-1}$.

Preferably there are a plurality of split/merge processors organized as a tree-type structure in a plurality of layers. The split/merge processors are operable to merge groups of calculated projection data subsets from the next lower layer to present a lesser number of calculated projection data subsets to the next higher layer, the lowest layer merging groups of the calculated projection data subsets $P_i^0$ through $P_i^{m-1}$ from the backproject/reproject processors, and the highest layer producing the calculated projection data set $P_i$. The split/merge processors are also operable to split one or more correction projection data subsets from the next higher layer to present a greater number of correction projection data subsets to the next lower layer, the highest layer splitting the correction data set $E_i$, and the lowest layer producing the correction projection data subsets $E_i^0$ through $E_i^{m-1}$.

At least the split/merge processors comprise transputers. The split/merge processors of each layer each include on I/O connected to the next higher layer, and three I/O parts connected to the next lower layer.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION

Figure 1:
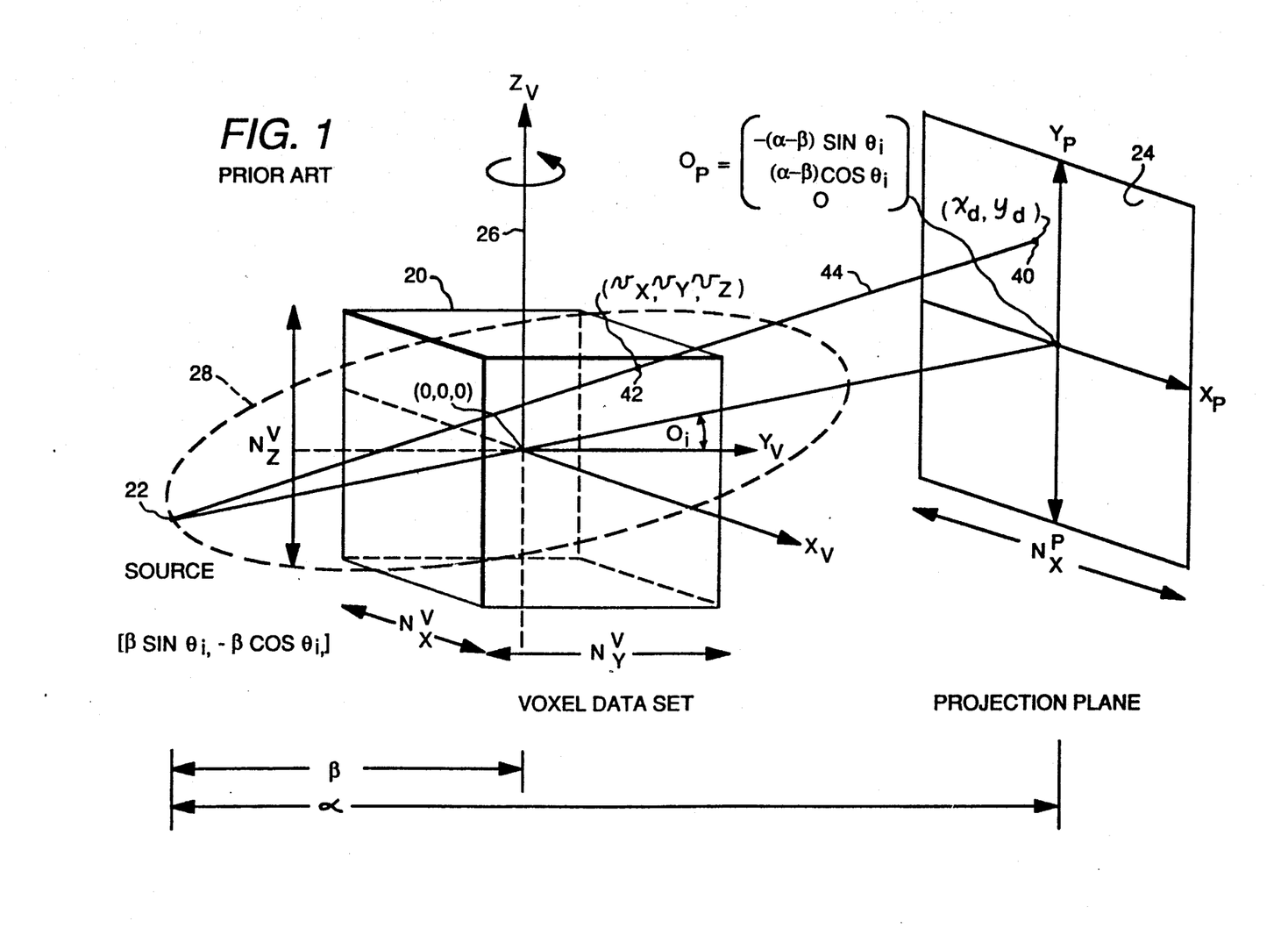
FIG. 1 depicts data acquisition employing cone beam geometry for scanning an object to acquire cone beam projection data, and additionally graphically depicts the geometry for backprojection and reprojection operations.

Referring first to FIG. 1, depicted in a typical scanning and data acquisition configuration employing cone beam geometry. A cube 20 alternatively represents an actual 3D object being scanned or a 3D voxel (volume element) data set V representing the actual object. The voxel data set V may be indexed, for example, by voxel number v. It will be appreciated that, during a scanning and data acquisition operation, the actual object is scanned with x-rays; and, during a subsequent image reconstruction operation, the voxel data set V is calculated to represent an image of the actual object. The present invention is directed to image reconstruction.

A global coordinate system $C_v^3 = (X,Y,Z,)$ is defined, with its origin (0,0,0) at the center of the voxel data set V or object 20. The object 20 is positioned within a field of view between a cone beam x-ray point source 22 and a 2D array detector 24, from which cone beam projection data is acquired. The 2D array detector 24 is connected to a conventional high speed data acquisition system (not shown). An axis of rotation 26 coincident with the $Z_v$ axis passes through the field of view and the object 20. Perpendicular to the $Z_v$ axis of rotation 26 is a midplane within which the $X_v$ and $Y_v$ axes lie, as well as a circular source scanning trajectory 28 centered on the $Z_v$ axis of rotation 26.

For scanning the object at a plurality of discrete source position $\theta_i$ on the source scanning trajectory 28, which in FIG. 1 are discrete angular positions $\theta_i$, the x-ray source 22 moves relative to the object 20 along the source scanning trajectory 28, while the 2D array detector 24 remains fixed in position relative to the source 22. Either the source 22 and detector 24 may be rotated around a stationary object 20, or the object 20 may be rotated while the source 22 and detector 24 remain stationary.

At each discrete source position $\theta_i$ a 2D measured cone beam pixel data set $P_i$ is acquired by the data acquisition system (not shown) connected to the array detector 24, and stored for subsequent reconstruction. Each measured cone beam pixel data set $P_i$ includes a plurality of pixels indexed, for example, by pixel number p.

Thus, in the particular geometry of FIG. 1, data are acquired at a number of angular positions or view angles $\theta_i$ around the object. As depicted, $\alpha$ is the source-to-detector distance and $\beta$ is the source-to-rotation-axis distance. For each view angle $\theta_i$, the x-ray source 22 is located at $[\beta\sin\theta_i, -\beta\cos\theta_i, 0]^T$ and a 2D projection $P_i$ is acquired. The center of the 2D projection array 24 is located at $0_p = [-(\alpha-\beta)\sin\theta_i, (\alpha-\beta)\cos\theta_i, 0]^T$.

Figure 2:
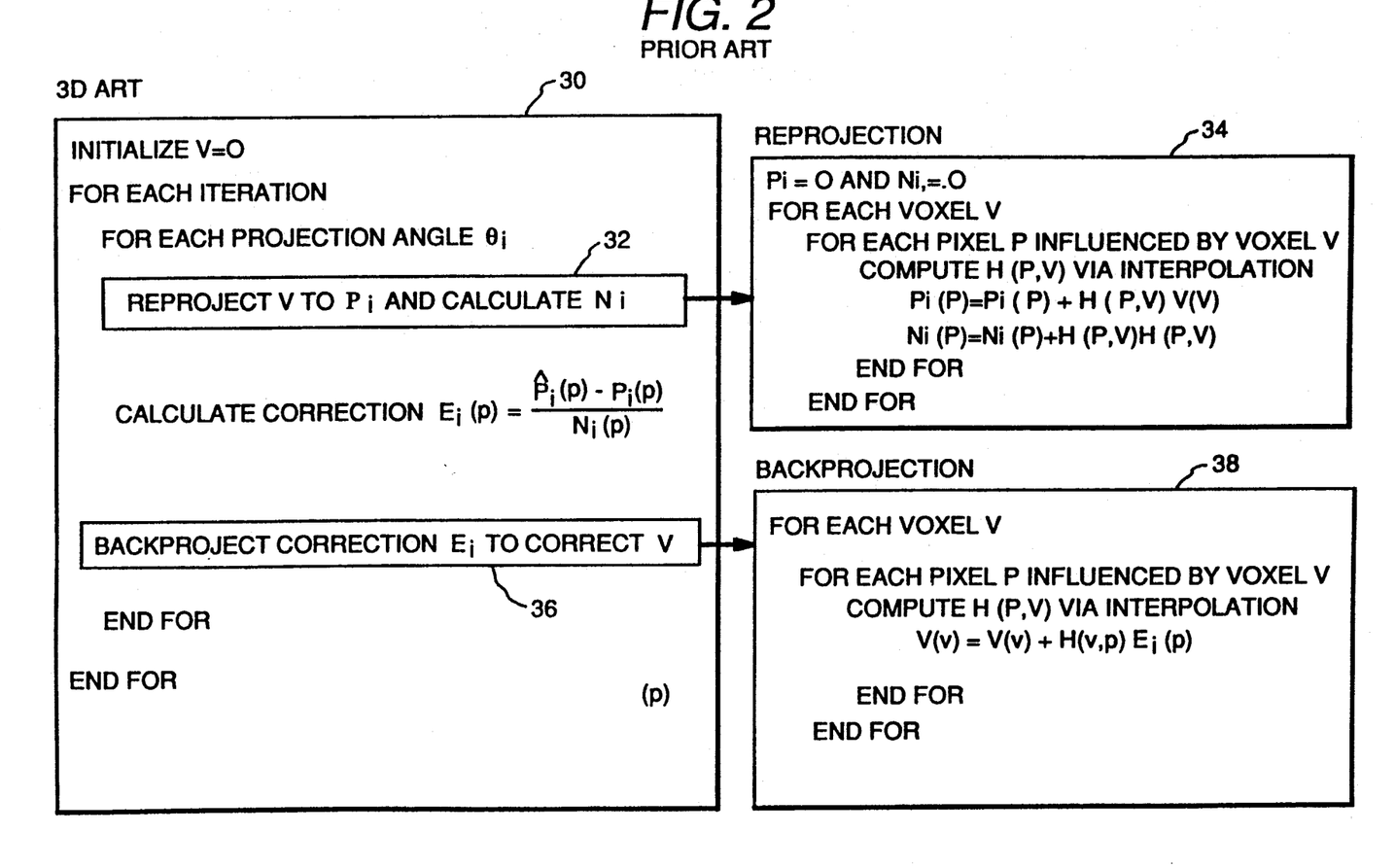
FIG. 2 represents the steps in the prior art 3D Algebra Reconstruction Technique (ART) for reconstruction.

FIG. 2 summarizes the procedure of the prior art three-dimensional Algebra Reconstruction Technique (ART), which is an iterative procedure using raysums to correct the value of each voxel of the 3D voxel data set V at each iteration. After a number of iterations, the values of the voxel data set V converge to represent the actual 3D object.

In box 30, the procedure commences by initializing the 3D voxel data set V, for example by clearing all voxel values to zero. The procedure then goes through successive iterations and, for each iteration, through each source position or projection angle $\theta_i$ corresponding to discrete angular positions on the source scanning trajectory 28. For each projection angle $\theta_i$ there are three steps: reprojection, error calculation and backprojection. The procedure is completed (not shown) either when a predetermined number of iterations have been processed, or when the error is below a predetermined threshold. The projection angles $\theta_i$ may be processed in any order, either sequentially or in some other order. Depending upon the particular scanning geometry, the order of projection angle $\theta_i$ processing can affect the rate of convergence of the voxel data set V.

Box 32 states the step of reprojection, which is in turn detailed in Box 34 in the manner of a subroutine. The 3D voxel data set V (or a selected portion of interest) is reprojected from real space to projection space to generate a 2D calculated projection data set $P_i$ for the particular projection angle $\theta_i$. The 2D calculated projection data set $P_i$ corresponds on a pixel-by-pixel basis with the actual measured cone beam pixel data set $P_i$, but with actual pixel data values differing depending upon how accurately the voxel data set V represents the actual object, and depending upon various inherent computational errors. In conjunction with the reprojection, a 2D normalizing factor data set $N_i$ is also calculated, corresponding on a pixel-by-pixel basis with the calculated and measured projection data sets $P_i$ and $P_i$.

Considering the reprojection process of Box 34 in detail, the calculated projection data set $P_i$ and the normalizing factor data set $N_i$ are each initialized by clearing all pixels to zero. Then for each voxel v of the 3D voxel data set V, each pixel p of the calculated projection data set $P_i$ and the corresponding normalizing factor data set $N_i$ influenced by the voxel is identified in a manner described hereinbelow with reference again to FIG. 1. For each pixel p so influenced by voxel v, the following three operations are performed: (1) A weighting factor h(p,v) for the particular voxel and pixel positions is determined based on geometry, for example by a well-known bi-linear interpolation process. (2) The value of the voxel V(v) is multiplied by the weighting factor h(p,v) and added to the value of the calculated projection data set pixel $P_i(p)$ such that pixel values are cumulated. (3) The weighting factor h(p,v) is multiplied by itself and added to the value of the normalizing factor dat set element $N_i(p)$ such that element values are cumulated.

Returning to Box 30 of FIG. 2, a 2D correction projection data set $E_i$ indexed, for example, by pixel number p, is calculated. For each pixel of the corresponding data sets, the difference between the value of the measured projection data set pixel $P_i(p)$ and the value of the corresponding calculated projection data set pixel $P_i(p)$ is determined, and then normalized by dividing by the value of the corresponding normalizing factor data set element $N_i(p)$. The result is the value of the corresponding correction projection data set element $E_i(p)$.

Box 36 states the step of backprojection, which is in turn detailed in Box 38 in the manner of a subroutine. The 2D correction projection data set $E_i$ for the particular projection angle $\theta_i$ is backprojected from projection space to real space to correct voxel values in the 3D voxel data set V.

Considering the backprojection process of Box 38 in detail, for each voxel v of the 3D voxel data set V, each pixel p of the correction projection data set $E_i$ influenced by the voxel is identified. For each pixel p so influenced by voxel v, the weighting factor h(p,v) is determined via interpolation based on geometry, and then the value of the correction projection data set pixel $E_i(p)$ is multiplied by the weighting factor h(p,v), and the product added to the value of the voxel value V(v), such that voxel values are cumulatively corrected.

Referring again to FIG. 1, the manner in which array detector pixels influenced by each voxel is determined will now be described in the context of the backprojection and reprojection procedures.

Let $V(x_v, y_v, z_v)$ represent a three-dimensional voxel data set defined in the three-dimensional discrete Cartesian coordinate system, $C_v^3$, with the origin located at the center of the 3D cubic data. For a 3D voxel data set with $(N_x^V \times N_y^V \times N_z^V)$ voxels, every voxel can be indexed by $(i_x, i_y, i_z)$. The coordinate of each voxel is stated as $$x_v = i_x \times \kappa_x \; i_x = -\frac{N_x^V}{2} + 1, \ldots, \frac{N_x^V}{2} - 1 \quad (1)$$

$$y_v = i_y \times \kappa_y \; i_y = -\frac{N_y^V}{2} + 1, \ldots, \frac{N_y^V}{2} - 1$$

$$z_v = i_z \times \kappa_z \; i_z = -\frac{N_z^V}{2} + 1, \ldots, \frac{N_z^V}{2} - 1$$

where $k_x$, $k_y$, and $k_z$ denote the voxel resolution along the x, y, and z axis in the coordinate system $C_v^3$, respectively. A two-dimensional discrete Cartesian coordinate system $C_{P\theta i}$ is used to address each detector element in the 2D area detector. Every detector element D(xd, yd) is indexed by $$x_d = j_x \times \mu_x \; j_x = -\frac{N_x^P}{2} + 1, \ldots, \frac{N_x^P}{2} - 1 \quad (2)$$

$$y_d = j_y \times \mu_y \; j_y = -\frac{N_y^P}{2} + 1, \ldots, \frac{N_y^P}{2} - 1$$

the $\mu_x$ and $\mu_y$ are used to indicate the detector resolution along the x and y axis, respectively. The relative relationship between $C_{P\theta}{}^2$ and $C_v{}^3$ can be stated as $4\times 4$ transformation function $T_{P\theta \to v}$. For each detector $P_{0i}(x_d, y_d)$ defined in the detector coordinate system $C_{P\theta}{}^2$, the coordinate $(x_d, y_d)$ can be transferred to the voxel coordinate system $C_v{}^3$ by applying the transformation function $T_{P\theta \to v}$, i.e., $$\begin{bmatrix} x \\ y \\ z \end{bmatrix} = [T_{P\theta_i \to v}] \begin{bmatrix} x_d \\ y_d \\ 0 \end{bmatrix} \quad (3)$$

transformation function $T_{P\theta \to v}$, which transfers the detector coordinate system to the voxel coordinate system, is expressed as rotating about the y axis by $\theta_i$, then rotating 90° around the reference x axis, and finally translating by $O_p$; i.e., $$T_{P\theta_i \to V} = Tran(O_p) Rot\left(x, \frac{\pi}{2}\right) Rot(y, \theta_i) \quad (4)$$

$$= \begin{bmatrix} 1 & 0 & 0 & -(\alpha - \beta)\sin\theta_i \\ 0 & 1 & 0 & (\alpha - \beta)\cos\theta_i \\ 0 & 0 & 1 & 0 \\ 0 & 0 & 0 & 1 \end{bmatrix} \begin{bmatrix} 1 & 0 & 0 & 0 \\ 0 & \cos\pi/2 & -\sin\pi/2 & 0 \\ 0 & \sin\pi/2 & \cos\pi/2 & 0 \\ 0 & 0 & 0 & 1 \end{bmatrix} \begin{bmatrix} \cos\theta_i & 0 & \sin\theta_i & 0 \\ 0 & 1 & 0 & 0 \\ -\sin\theta_i & 0 & \cos\theta_i & 0 \\ 0 & 0 & 0 & 1 \end{bmatrix}$$

$$= \begin{bmatrix} \cos\theta_i & 0 & \sin\theta_i & -(\alpha - \beta)\sin\theta_i \\ \sin\theta_i & 0 & -\cos\theta_i & (\alpha - \beta)\cos\theta_i \\ 0 & 1 & 0 & 0 \\ 0 & 0 & 0 & 1 \end{bmatrix}$$

where $\theta_i$ is View angle measured respect to the y axis in $C_v^3$
$\alpha$ is Source to detector distance (STOD)
$\beta$ is Source to rotation axis distance (STOD) then Equation (3) can be rewritten as $$\begin{bmatrix} x \\ y \\ z \end{bmatrix} = \begin{bmatrix} \cos\theta & 0 & \sin\theta_i & -(\alpha - \beta)\sin\theta_i \\ \sin\theta_i & 0 & -\cos\theta_i & (\alpha - \beta)\cos\theta_i \\ 0 & 1 & 0 & 0 \\ 0 & 0 & 0 & 1 \end{bmatrix} \begin{bmatrix} x_d \\ y_d \\ 0 \end{bmatrix} \quad (5)$$

i.e., $$\begin{cases} x = x_d\cos\theta_i - (\alpha - \beta)\sin\theta_i \\ y = x_d\sin\theta_i + (\alpha - \beta)\cos\theta_i \\ z = y_d \end{cases} \quad (6)$$

For each voxel $V(x_v, y_v, z_v)$, given a view angle $\theta_i$, an integration line such as an exemplary integration line 44 passes through the x-ray source 22 located at $[\beta\sin\theta_i, -\beta\cos\theta_i, 0]^T$ and voxel $V(x_v, y_v, z_v)$, can be expressed as $$\frac{x - \beta\sin\theta_i}{x_v - \beta\sin\theta_i} = \frac{y + \beta\cos\theta_i}{y_v + \beta\cos\theta_i} = \frac{z}{z_v} \quad (7)$$

where (x,y,z) is any point belonging to the integration line 44. This integration line 44 intersects the detector plane at the location $(x_d, y_d)$ in the projection coordinate system. Substituting Equation (6) into Equation (7) yields $$\frac{x_d\cos\theta_i - (\alpha - \beta)\sin\theta_i - \beta\sin\theta_i}{x_v - \beta\sin\theta_i} =$$

$$\frac{x_d\sin\theta_i + (\alpha - \beta)\cos\theta_i + \beta\cos\theta_i}{y_v + \beta\cos\theta_i} = \frac{y_d}{z_v}$$

Then the intersection point $(x_d, y_d)$ on the detector or projection plane can be calculated as $$x_d = \frac{\alpha[x_v\cos\theta_i + y_v\sin\theta_i]}{y_v\cos\theta_i - x_v\sin\theta_i + \beta}$$

$$y_d = \frac{\alpha z_v}{y_v\cos\theta_i - x_v\sin\theta_i + \beta}$$

A voxel-driven approach is applied for both backprojection and reprojection. At a given view angle $\theta_i$, a unique intersection point $(x_d, y_d)$ on the detector plane $C_{P_0}{}^2$ can be calculated for a given voxel $(x_v, y_v, z_v)$ in $C_v{}^3$, as represented in FIG. 1 by the intersection point 40 and voxel 42 along line 44. Four immediate neighbor pixels surrounded the intersection point $(x_d, y_d)$. By a known process of bilinear interpolation, weighting factors reflecting the contribution of each voxel to each pixel on the detector plane can be calculated for reprojection, and weighting factors reflecting the contribution of each pixel on the detector plane to each voxel can be calculated for backprojection.

Figure 3:
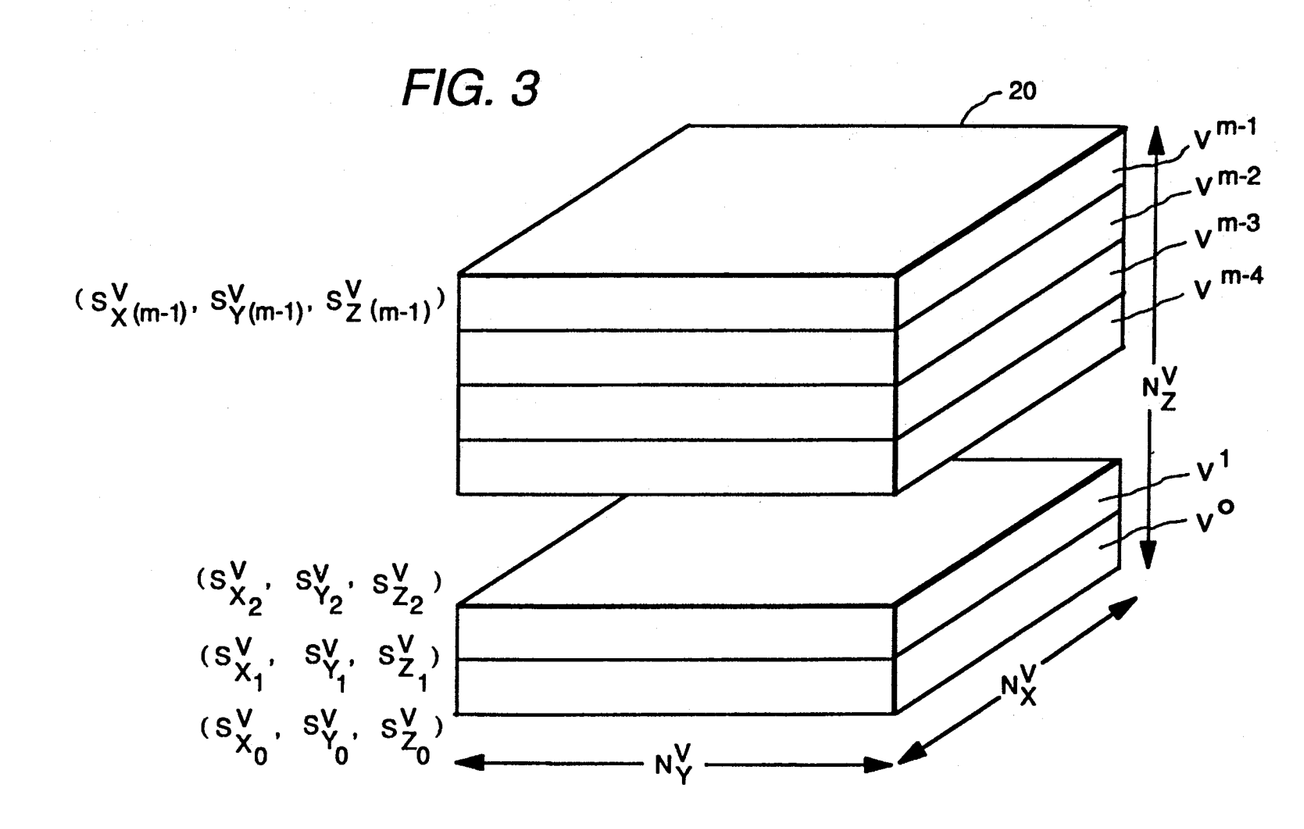
FIG. 3 depicts the organization of a 3D voxel data set into independent voxel subcubes.

With reference now to FIG. 3, the 3D voxel data set V (or 20 in FIG. 1) is organized as a plurality m of independent voxel subcubes $V^0$ through $V^{m-1}$. The voxel subcubes are independent in the sense that no overlapping region exists between adjacent voxel subcubes. While the voxel data set may be divided in a variety of ways, preferably boundaries between adjacent voxel subcubes lie in planes which are perpendicular to the detector planes and parallel to each other, as depicted in FIG. 3. The size of each voxel subcube is constrained by the memory space associated with each processor element used to do back projection and reprojection, described hereinbelow with reference to FIGS. 5, 8 and 9.

Figure 4:
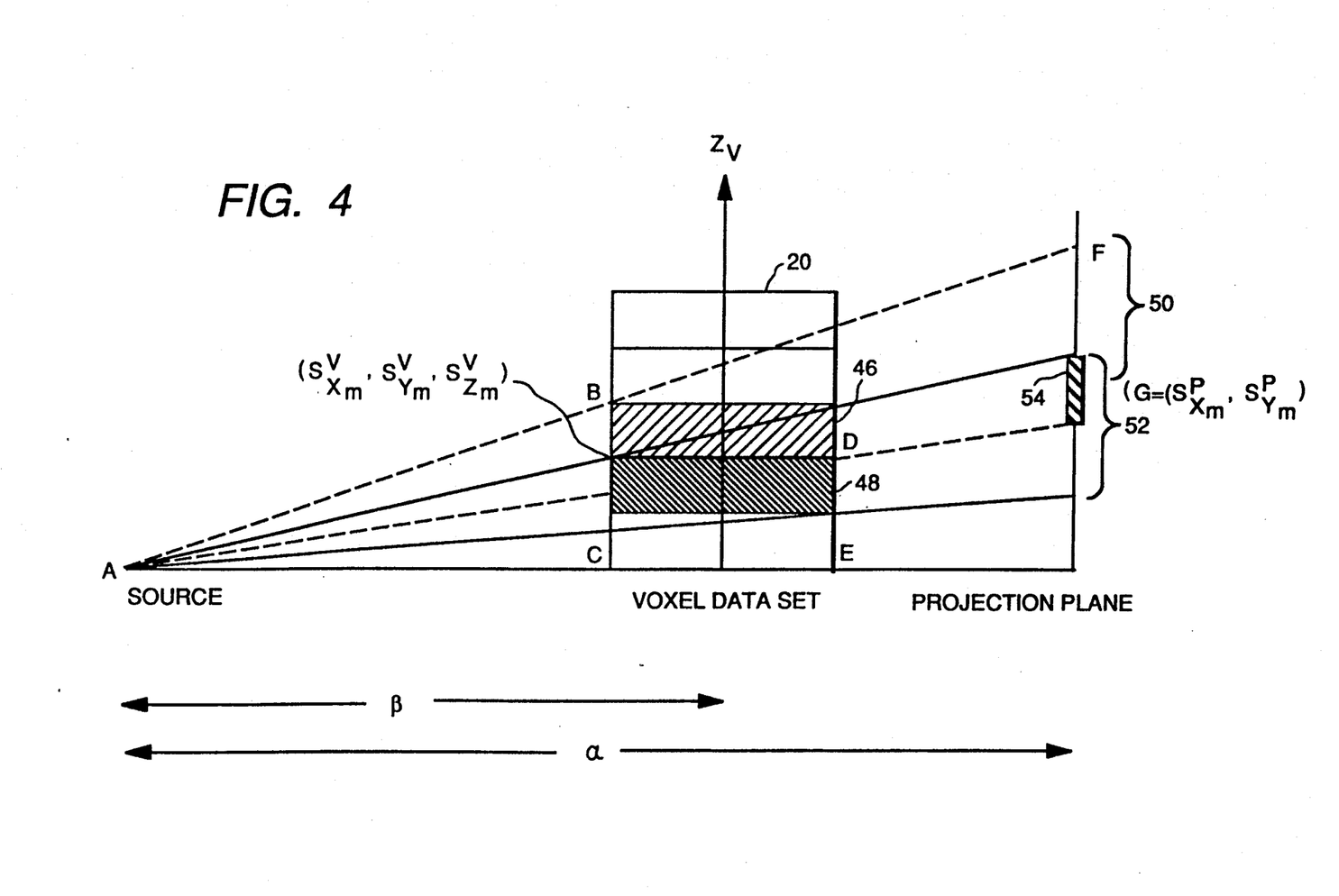
FIG. 4 depicts the geometry relationship between voxel subcubes and projection strips or subsets.

FIG. 4 depicts the geometric relationship between the voxel subcubes of FIG. 3 and projections on the detector array for each angular position $\theta_i$. For each voxel subcube in real space there is a corresponding projection subset on the projection plane. In the planar arrangement of voxel subcubes illustrated, the projection subsets take the form of parallel strips on the detector plane.

Thus, in FIG. 4 there are two representative voxel subcubes 46 and 48, with corresponding projection strips 50 and 52. There is an overlapping region 54 between the two projection strips 50 and 52. It is however a feature of the invention that each voxel subcube and its corresponding projection strip can be projected and reprojected in parallel with other pairs of voxel subcubes and projection strips without interference.

Figure 5:
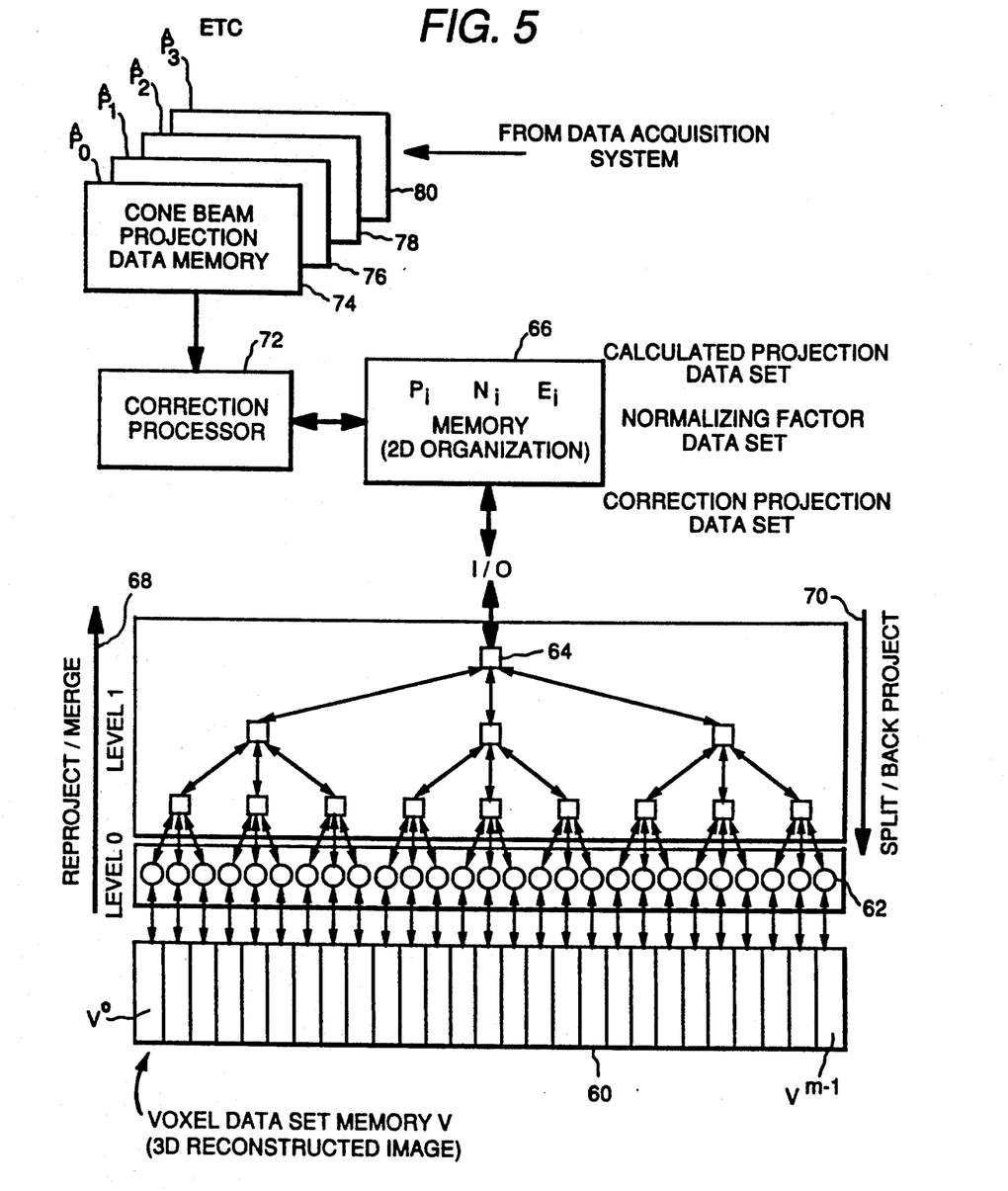
FIG. 5 is a black diagram of apparatus implementing ART in accordance with the invention.

FIG. 5 depicts apparatus in accordance with the invention, comprising a bi-level parallel processor architecture. Included in the FIG. 5 apparatus is a data memory 60 for storing the 3D voxel data set V, organized as indicated into separate memory areas for each of the independent voxel subcubes $V^0$ through $V^{m-1}$.

In a level 0 are a plurality of m of backproject/reproject processors, such as processor 62, corresponding respectively to the voxel subcubes. Each of the backproject/reproject processors of level 0 operates independently of an in parallel with the other processors of level 0 to reproject and backproject back and forth between a particular voxel subcube and a particular projection strip as part of the overall iterative process.

In a level 1 is at least one, and preferably many, split/merge processor, such as processor 64. Using 4-link connectable processors, such as the INMOS T800 transputer, processors in level 1 are organized in layers in a tree-type manner. Each level 1 processor (or node) has three sons and one parent in the particular embodiment illustrated. The INMOS T800 transputer is basically a computer on a chip with a 32-bit integer processor and a 64 bit floating point processor, with a practically achievable floating point computation rate of approximately 1.5 MFLOPS. It includes 4 kBytes of on-chip memory, and address space for 4 Gbytes of off-chip memory. Each transputer can be connected to four neighbors over a point-to-point link with a 20-Mbit/second bandwidth. An available development system, namely a Meiko Computing Surface, includes 512 transputers, with a maximum computation rate of approximately 800 MFLOPS.

The level 1 processors are operable, following a level 0 reproject operation, which produces m calculated projection data subsets $P_i^0$ through $P_i^{m-1}$, to merge the calculated projection data subsets $P_i^0$ through $P_i^{m-1}$ into a memory 66, as well as to merge normalizing factor data subsets $N_i^0$ through $N_i^{m-1}$ from the level 0 processors into a single normalizing factor data set $N_i$ for storing in the memory 66. The level 1 processors are also operable to split a correction projection data set $E_i$ stored in the memory 66 into a plurality of correction projection data subsets $E_i^0$ through $E_i^{m-1}$ for backprojection by the level 0 processors. In FIG. 5, the arrows 68 and 70 respectively indicate these two types of operation, namely, reproject then merge, and split then backproject.

Also shown in FIG. 5 is a correction processor 72 which operates in a conventional manner as described hereinabove to calculate the correction projection data set $E_i$ based on the difference between the calculated projection data set $P_i$, and the measured projection data set $P_i$ for the particular projection angle $\theta_i$. The measured projection data sets $P_i$ resulting from data acquisition as described hereinabove with reference to FIG. 1 are stored in exemplary memories 74, 76, 78 and 80.

Thus, one projection array is associated with each split/merge processor in level 1. During backprojection, each split/merge processor reads in a projection reads in a projection strip from its parent node, splits it into three projection substrips, and then distributes those to its son nodes for further splitting or backprojection. During reprojection, each split/merge processor reads in three projection strips from its son nodes (either the backproject/reproject processors or split/merger processors), merges them into one projection strip, and sends that projection strip to its parent node for further merging. The number of processor layers in level 1 is related to the total number of backproject/reproject processors in level 0. One voxel subcube and its corresponding projection strip are associated with each backproject/reproject processor in level 0. During backprojection, each split/merge processor reads in a projection strip from its parent node and splits it into three projection substrips, and then distributes those to its son nodes. Each backproject/reproject processor receives a projection strip from its parent node and performs voxel-driven backprojection. During reprojection, each backproject/reproject processor calculates a projection strip for the desired view angle and sends the resulting projection strip to its parent node (split/merge processor) for merging. The 3D algebra Reconstruction Technique is achieved by iteratively performing backprojection and reprojection. The entire parallel processing procedure of the 3D cone beam algebra reconstruction algorithm can be divided into four major tasks: split, merge, backproject, and reproject.

Figure 6:
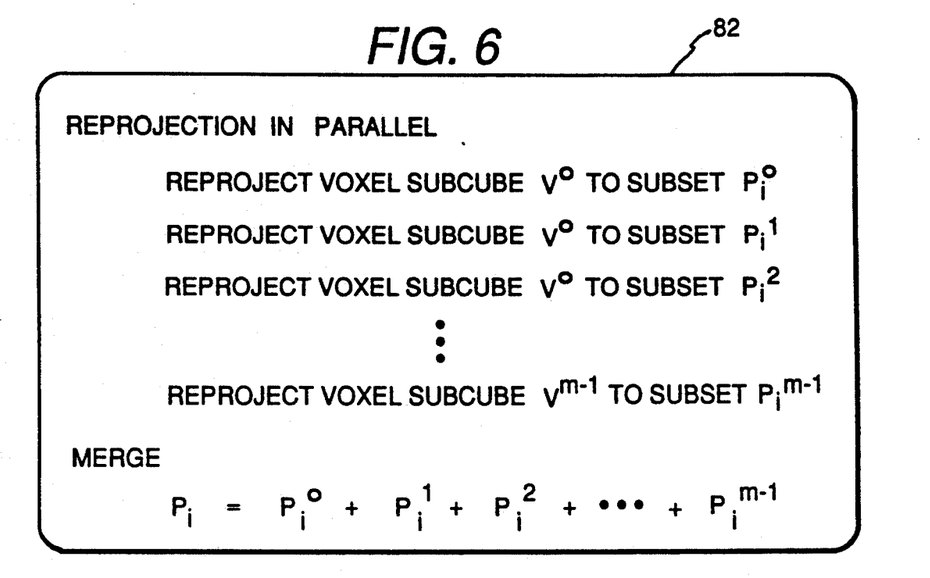
FIG. 6 represents the steps of reprojection and merge in the ART implementation of the invention.
Figure 7:
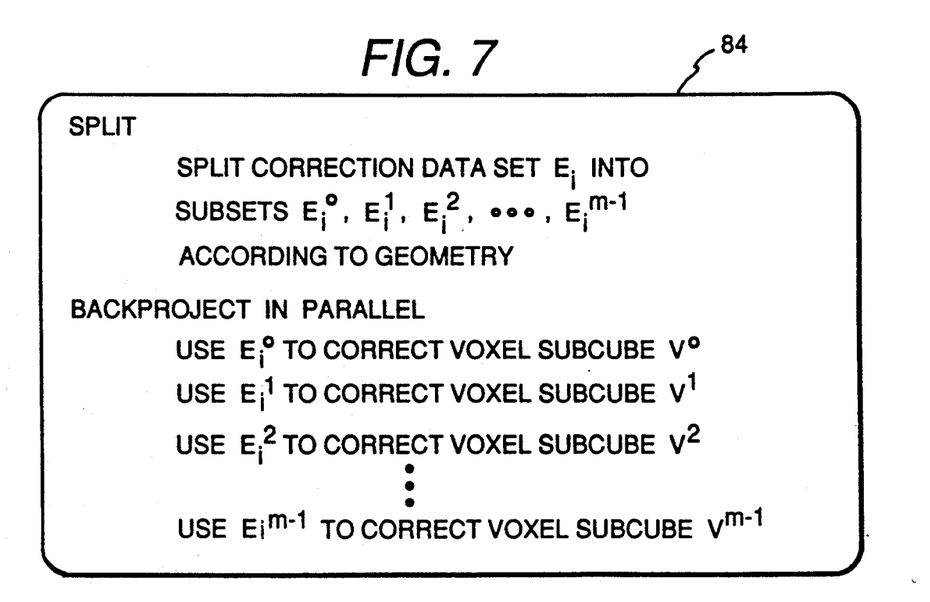
FIG. 7 represents the steps of split and backproject in the ART implementation of the invention.

These four tasks are represented in Boxes 82 and 84 of FIGS. 6 and 7. In the ART implementation of the invention, the reprojection and merge tasks in Box 82 of FIG. 6 are substituted for the prior art reprojection step represented in Box 34 of FIG. 2. Similarly, the split and backproject tasks in Box 84 of FIG. 7 are substituted for the prior art backprojection step represented in Box 38 of FIG. 2. The four tasks will now be considered in detail in the order presented in the Boxes 82 and 84.

The reproject process is executed by each backproject/reproject processor in level 0 or reprojection. Its primary function is to generate a projection strip for a given view angle from a voxel subcube and send the results to its parent node for projection merging. The reprojection procedure uses a voxel-driven approach and is illustrated as follows:

```
for a given view angle θ_i
    set P = 0 and N = 0
    for each voxel v in the voxel subcube
        calculate pixel location in the projection
        strip influenced by v for each
        pixel p influenced by v
            calculate h(v,p), the weighting
            factor, via interpolation
            P(p) = P(p) + h(p,v)V(v)
            N(p) = N(p) + H(p,v)h(p,v)
        end for
    end for
end for
```

Figure 8:
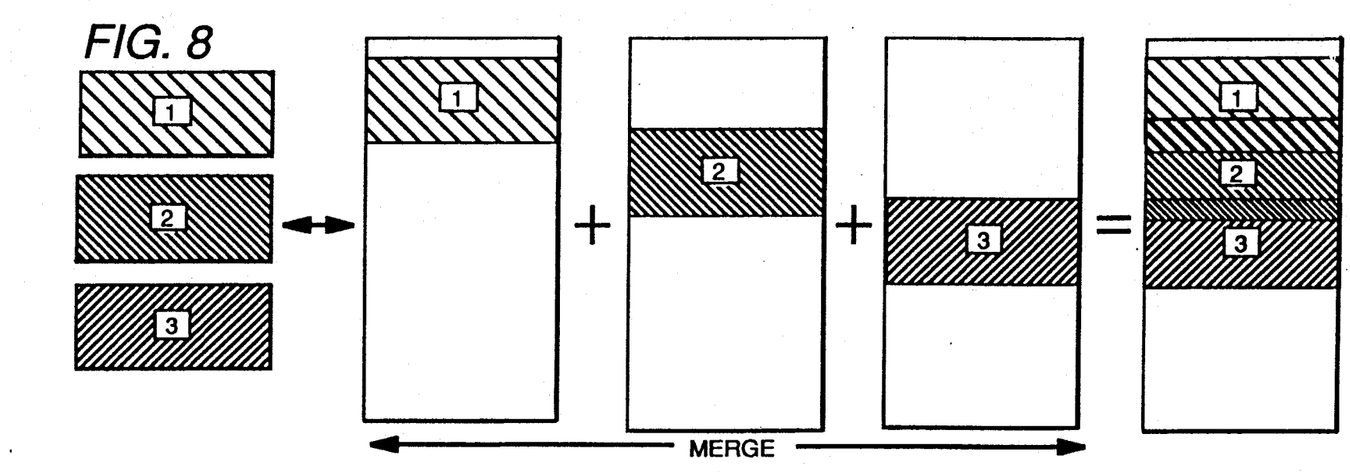
FIG. 8 depicts the merging of projection strips or subsets.

The merge process runs on the split/merge processors in level 1 for reprojection purposes. Its primary function is to merge three projection strips, read from its three son nodes, into one. As mentioned hereinabove, an overlapping region between two projection strips corresponds to two adjacent voxel subcubes. The merge is achieved by adding projection strips together in the overlapping region according to its global coordinate system, as represented in FIG. 8.

Figure 9:
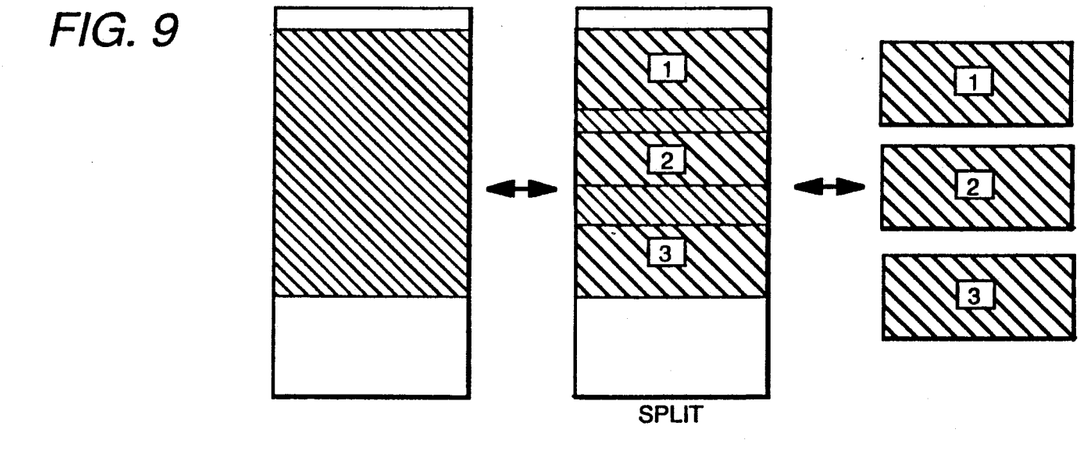
FIG. 9 depicts splitting into projection strips or subsets.

The split process is executed by the split/merge processors in level 1 for backprojection. Its primary function is to partition the projection strip into three projection substrips according to the global location of the voxel subcubes processed by its son nodes. As mentioned hereinabove, an overlapping region exists between projection strips that corresponds to two adjacent voxel subcubes. Projection data in the overlapping region are duplicated in two adjacent projection strips, as represented in FIG. 9. Before performing projection splitting, the processor reads in projection strips from its parent node and reads in information from its son nodes about the starting point and dimensions of the voxel sector of its son nodes. Then the input projection strip is divided into three projection substrips, according to the global location of the voxel subcubes processed by its son nodes and the scanning geometry, and the resulting three projection strips are distributed to its son nodes. The backproject process is executed by the backproject/reproject processors in level 0 for backprojection. Its primary function is to read in a projection strip for every view angle and backproject it to a voxel subcube. The backprojection procedure uses a voxel-driven approach and is illustrated as follows:

```
for every view angle θ_i
    read in projection strip from its parent node
    for each voxel v in the voxel subcube
        calculate pixel location in the projection
        strip influenced by v for each
        pixel p influenced by v
            calculate h(v,p), the weighting
            factor, via interpolation
            V(v) = V(v) + h(v,p)P(v)
            N(p) = N(p) + h(p,v)h(p,v)
        end for
    end for
end for
```

Considering the parallel processing approach in detail with reference to the geometry of FIGS. 1, 3 and 4, an $(N_Z^V \times N_Y^V \times N_X^V)$ voxel data set can be divided into (M) voxel subcubes, each with $[(N_Z^V/M) \times N_Y^V \times N_X^V]$ voxels. The starting pint of each voxel subcube is stated as $$[S_{Xm}^V, S_{Ym}^V, S_{Zm}^V] = \left[ -\frac{N_X^V}{2}, -\frac{N_Y^V}{2}, -\frac{N_Z^V}{2} + \left(\frac{N_Z^V}{M}\right)m \right]$$

for m=0, .. (M−1). The variable m is used to denote the voxel subcube index. For each voxel subcube, its corresponding region on the projection plane that may contribute to it can be identified according to the scanning geometry. There are M projection strips corresponding to voxel subcubes. The starting point of the projection strip corresponding to the $m^{th}$ voxel subcube is stated as $$[S_{Xm}^P, S_{Ym}^P] = \left[ 0, \frac{(S_{Zm}^V)\alpha}{\beta + (N_Y^V/2)} \right]$$

and each projection strip contains $$N_X^P \times \left| \frac{(S_{Zm}^V + 1 - 1)\alpha}{[\beta - (N_Y^V/2)]} - \frac{(S_{Zm}^V)\alpha}{[\beta + (N_Y^V/2)]} \right|$$

projection elements. The variable $N_X^P$ denotes the number of detector elements along the x axis of the projection coordinate system. The geometric relationship between the starting point of each voxel subcube and the starting point of its corresponding projection strip is illustrated in FIG. 4.

Each voxel in a voxel subcube handled by a backproject/reproject processor is indexed by ($i_v, j_v, k_v$), where $$i_v = 0, \ldots, (N_X^V - 1)$$
$$j_v = 0, \ldots, (N_Y^V - 1)$$
$$k_v = 0, \ldots, \left(\frac{N_Z^V}{M} - 1\right)$$

Its global coordinate can be calculated as $$V_X = (S_X^V + i_v) \times R_V^x$$
$$V_Y = (S_Y^V + j_v) \times R_V^y$$
$$V_Z = (S_Z^V + k_v) \times R_V^z$$

The voxel resolutions along the x, y, and z axes are specified as ($R_V^x, R_V^y, R_V^z$). The integration line connecting the x-ray source and the voxel ($V_X, V_Y, V_Z$) for the view angle $\theta_i$ can be stated as $$\frac{x - \beta\sin\theta_i}{V_x - \beta\sin\theta_i} = \frac{y + \beta\cos\theta_i}{V_y - \beta\cos\theta_i} = \frac{z}{V_Z}$$

This integrating line will intersect the detector plane at the location ($X_d, Y_d$) in the projection coordinate system show in FIG. 4.

$$X_d = \frac{\alpha[V_X\cos\theta_i + V_Y\sin\theta_i]}{V_Y\cos\theta_i - V_X\sin\theta_i + \beta}$$

$$Y_d = \frac{\alpha V_Z}{V_Y\cos\theta_i - V_X\sin\theta_i + \beta}$$

In order to reduce computation, the ($X_d$, $Y_d$) can be calculated as follows:

$$X_d = \frac{\alpha A}{B}$$

$$Y_d = \frac{\alpha C}{B}$$

where $$\begin{cases} A = A_0 + i_v(R_V^x\cos\theta_i) + j_v(R_V^y\sin\theta_i) \\ B = B_0 - i_v(R_V^x\sin\theta_i) + j_v(R_V^y\cos\theta_i) \\ C = C_0 + k_v R_V^z \end{cases}$$

and $$\begin{cases} A = S_X^V R_V^x\cos\theta_i + S_Y^V R_V^y\sin\theta_i \\ B = S_Y^V R_V^y\cos\theta_i - S_X^V R_V^x\sin\theta_i + \beta \\ C_0 = S_Z^V R_V^z \end{cases}$$

The values A, B, and C can be calculated by incrementing their values with a constant increment. This approach significantly reduces the computation complexity of calculating $X_d$ and $Y_d$. Then a bi-linear interpolating scheme is applied to calculate the weighting factor for all the pixels influenced by the voxel ($V_X, V_Y, V_Z$). The computation of the pixel location ($X_d, Y_d$) is unique and applicable to both the back projecting and the reprojection cases. The bi-level tree-type parallel-processor architecture and the four major processing tasks (split, merge, backproject, and reproject) are implemented on the Meiko Computing Surface (T800 transputer development system). Each backproject/reproject processor of each split/merge processor (FIG. 5) is mapped to a T800 transputer.

While the illustrated embodiment employs a geometry wherein there is overlap only between two adjacent projection strips or subsets, it will be appreciated that more than two projection strips or subsets may overlap. Similarly, each FIG. 5 split/merge processor in level 1 has one parent node and three son nodes, which facilitates implementation with transputers which have four I/O parts. However, different numbers of son nodes may be employed. Moreover, rather than a three-type architecture, level 1 may comprise a single processor which merges all projection strips or subsets in a single operation, or correspondingly splits the complete projection data set into a plurality of projection strips or subsets in one operation.

This technique can be applied to both medical and industrial 3D CT imaging. Because it is based on a voxel-driven algebraic reconstruction technique, it is particularly useful for reconstructing regions of interest. The parallelism provided by the Split and Merge Reconstruction method can be extended to large data sets. Performance improves as the number of backproject/reproject processors grows.

While specific embodiments of the invention have been illustrated and described herein, it is realized that modifications and changes will occur to hose skilled in the art. It is therefore to be understood that the appended claims are intended to cover all such modifications and changes as fall within the true spirit and scope of the invention.

What is claimed is:

1. A parallel processing method based on the Algebra Reconstruction Technique (ART) for iteratively reconstructing from cone beam projection data a 3D voxel data set V representing an image of an object, said method comprising:

irradiating the object using a cone beam x-ray source to obtain cone beam projection data on a two-dimensional array detector by scanning the object along a source scanning trajectory to obtain, at each of a plurality of discrete source positions $\theta_i$ on the source scanning trajectory, a 2D measured cone beam pixel data set $P_i$;

organizing the voxel data set V as a plurality m of independent voxel subcubes $V^o$ through $V^{m-1}$, each voxel subcube including a plurality of voxels; initializing the voxel data set V; and performing successive iterations to correct values of at least selected voxels of the 3D voxel data set based on the measured cone beam data sets $P_i$, during each iteration correcting the values of at least the selected voxels for each of the discrete source positions $\theta i$ on the source scanning trajectory by reprojecting each voxel subcube $V^o$ through $V^{m-1}$ to calculate pixel values for a corresponding 2D calculated projection data subset from a group of calculated projection data sets $i^{p0}$ through $i^{pm-1}$ of a 2D calculated projection data set $P_i$ including a plurality of pixels, the projection data subsets $i^{p0}$ through $i^{pm-1}$ overlapping in part merging the calculated projection data subsets $i^{P0}$ through $i^{Pm-1}$ to calculate pixel values of the 2D calculated projection data set $P_i$, the step of merging including adding pixel values in any overlapping regions of the calculated projection data subsets $i^{P0}$ through $P_i^{m-1}$, calculating a 2D correction projection data set $E_i$ including a plurality of pixels by determining the normalized difference between the value of each pixel of the measured projection data set $P_i$ and the value of the corresponding pixel of the calculated projection data set $P_i$, splitting the 2D correction projection data set $E_i$ into a plurality of 2D correction projection data subsets $i^{E0}$ through $i^{Em-1}$ corresponding to the voxel subcubes $V^o$ through $V^{m-1}$. the 2D correction projection data subsets $i^{E0}$ through $i^{Em-1}$ overlapping in part, and the step of splitting including duplicating element values for any overlapping regions of the correction projection data subsets $i^{E0}$ through $i^{Em-1}$. and backprojecting each correction projection data subsets $i^{E0}$ through $i^{Em-1}$ to correct voxel values in the corresponding voxel subcube of the plurality of voxel subcubes $V^o$ through $V^{m-1}$.

2. A method in accordance with claim 1, wherein:

the step of merging is organized in a tree-type manner as a plurality of layers and comprises, for each layer, merging groups of calculated projection data subsets from the next lower layer to present a lesser number of calculated projection data subsets to the next higher layer, the lowest layer merging groups of the calculated projection data subsets $P_i^0$ through $P_i^{m-1}$. from the step of reprojecting, and the highest layer producing the calculated projection data set $P_i$; and the step of splitting is organized in a tree-type manner as a plurality of layers and comprises, for each layer, splitting one or more correction projection data subsets from the next higher layer to present a greater number of correction projection data subsets to the next lower layer, the highest layer splitting the correction data set $E_i$, and the lowest layer producing the correction projection data subsets $E_i^0$ through $E_i^{m-1}$.

3. A method in accordance with claim 1, which comprises employing a plurality m of backproject/reproject processors corresponding to the voxel subcubes to perform the steps of reprojecting and backprojecting.

4. A method in accordance with claim 2, which comprises employing a plurality of split/merge processors connected in a tree structure to perform the steps of merging and splitting.

5. A method in accordance with claim 1, which further comprises, during each iteration, for each of the discrete source positions $\theta_i$:

in conjunction with the step of reprojecting each voxel subcube $V^o$ through $V^{m-1}$. calculating data values for a corresponding 2D normalizing factor data subset from a group of 2D normalizing factor subsets $N_i^0$ through $N_i^{m-1}$ of a 2D normalizing factor data set $N_i$ including a plurality of pixels, the 2D normalizing factor subsets $N_i^0$ through $N_i^{m-1}$ overlapping in part;

merging the normalizing factor data subsets $N_i^0$, through $N_i^{m-1}$ to calculate element values of the 2D normalizing factor data set $N_i$; and during the step of calculating the 2D correction data set $E_i$, employing each corresponding element of the normalizing factor data set element $N_i$.

6. A method in accordance with claim 1, wherein the step of reprojecting is voxel driven and comprises, for each voxel subcube of the plurality of voxel subcubes $V^o$ through $V^{m-1}$. :

initializing the corresponding calculated projection data subset from the group of projection data subsets $P_i^0$ through $P_i^{m-1}$. ; and for each of the selected voxels of the 3D voxel data set V included in the particular voxel subcube, adding to the value of each pixel of the corresponding calculated projection data subset from the group of calculated projection data subsets $P_i^0$ through $P_i^{m-1}$ influenced by the selected voxel the voxel value multiplied by a weighting factor h(p,v) determined for the voxel and pixel positions based on geometry such that pixel values are cumulated in the corresponding artificial projection data subset.

7. A method in accordance with claim 5, wherein the step of reprojecting is voxel driven and comprises, for each voxel subcube of the plurality of voxel subcubes $V^o$ through $V^{m-1}$. :

initializing the corresponding calculated projection data subset from the group of projection data subsets $P_i^0$ through $P_i^{m-1}$. ;

initializing the corresponding normalizing factor data subset from the group of normalizing factor data subsets $N_i^0$ through $N_i^{m-1}$. ; and for each of the selected voxels of the 3D voxel data set V(v) included in the particular voxel subcube, adding to the value of each pixel of the corresponding calculated projection data subset from the group of calculated projection data subsets $P_i^0$ through $P_i^{m-1}$ influenced by the selected voxel and voxel value multiplied by a weighting factor h(p,v) determined for the voxel and pixel positions based on geometry such that pixel values are cumulated in the corresponding artificial projection data subset, and adding to the value of each element of the corresponding normalizing factor data subset from the group of normalizing factor data subsets $N_i^0$ through $N_i^{m-1}$ the square of the weighting factor h(p,v) determined for the voxel and pixel positions based on geometry such that element values are cumulated in the corresponding normalizing factor data subset.

8. A method in accordance with claim 1, wherein the step of backprojecting is voxel driven and comprises, for each voxel subcube of the plurality of voxel subcubes $V^o$ through $V^{m-1}$.

for each of the selected voxels of the 3D voxel data set V included in the particular voxel subcube, adding to the voxel value the value of each element of the corresponding 2D correction projection data subset of the group of correction projection data subsets $E_i^0$ through $E_i^{m-1}$ in a pixel position influenced by the selected voxel multiplied by a weighting factor h(p,v) determined for the voxel and pixel positions based on geometry such that corrected voxel values are cumulated.

9. A method in accordance with claim 6, wherein the step of backprojecting is voxel drivel and comprises, for each voxel subcube of the plurality of voxel subcubes $V^o$ through $V^{m-1}$, for each of the selected voxels of the 3D voxel data set V included in the particular voxel subcube, adding to the voxel value the value of each element of the corresponding 2D correction projection data subset of the group of correction projection data subsets $E_i^0$ through $E_i^{m-1}$ in a pixel position influenced by the selected voxel multiplied by the weighting factor h(p,v) determined for the voxel and pixel positions based on geometry such that corrected voxel values are cumulated.

10. A method in accordance with claim 1, wherein the step of backprojecting is voxel driven and comprises, for each voxel subcube of the plurality of voxel subcubes $V^0$ through $V^{m-1}$, for each of the selected voxels of the 3D voxel data set V included in the particular voxel subcube, adding to the voxel value the value of each element of the corresponding 2D correction projection data strip of the group of correction projection data strips $E_i^0$ through $E_i^{m-1}$ in a pixel position influenced by the selected voxel multiplied by a weighting factor h(p,v) determined for the voxel and pixel positions based on geometry such that corrected voxel values are cumulated.

11. A parallel processing method based on the Algebra Reconstruction Technique (ART) for iteratively reconstructing from cone beam projection data a 3D voxel data set V representing an image of an object, the cone beam projection data acquired by employing a cone beam x-ray source and a two-dimensional array detector to scan the object along a circular source scanning trajectory lying in a plane perpendicular to a rotation axis passing through the object and perpendicular to all planes of the detector to obtain, at each of a plurality of discrete angular positions $\theta_i$ on the source scanning trajectory, a 2D measured cone beam pixel data set $P_i$, said method comprising:

organizing the voxel data set V as a plurality m of independent voxel subcubes $V^0$ through $V^{m-1}$, boundaries between adjacent voxel subcubes lying in planes perpendicular to all planes of the detector and parallel to each other, and each voxel subcube including a plurality of voxels;

initializing the voxel data set V; and performing successive iterations to correct the values of at least selected voxels of the 3D voxel data set based on the measured cone beam data sets $P_i$, during each iteration correcting the values of at least the selected voxels for each of the discrete angular positions $\theta_i$ on the source scanning trajectory by reprojecting each voxel subcube $V^0$ through $V^{m-1}$ to calculate pixel values for a corresponding 2D calculated projection data strip from a group of calculated projection data strips $P_i^0$ through $P_i^{m-1}$ of a 2D calculated projection data set $P_i$, the projection data strips $P_i^0$ through $P_i^{m-1}$ overlapping in part, merging the calculated projection data strips $P_i^0$ through $P_i^{m-1}$ to calculate pixel values of the 2D calculated projection data set $P_i$, the step of merging including adding pixel values in any overlapping regions of the calculated projection data strips $P_i^0$ through $P_i^{m-1}$ calculating a 2D correction projection data set $E_i$ by determining the normalized difference between the value of each pixel of the measured projection data set $P_i$ and the value of the corresponding pixel of the calculated projection data set $P_i$, splitting the 2D correction projection data set $E_i$ into a plurality of 2D correction projection data strips $E_i^0$ through $E_i^{m-1}$ corresponding to the voxel subcubes $V^0$ through $V^{m-1}$, the 2D correction projection data strips $E_i^0$ through $E_i^{m-1}$ overlapping in part, and the step of splitting including duplicating element values for any overlapping regions of the correction projection data strips $E_i^0$ through $E_i^{m-1}$, and backprojecting each correction projection data strip $E_i^0$ through $E_i^{m-1}$ to correct voxel values in the corresponding voxel subcube of the plurality of voxel subcubes $V^0$ through $V^{m-1}$.

12. A method in accordance with claim 11, wherein:

the step of merging is organized in a tree-type manner as a plurality of layers and comprises, for each layer, merging groups of calculated projection data strips from the next lower layer to present a lesser number of calculated projection data strips to the next higher layer, the lowest layer merging groups of the calculated projection data strips $P_i^0$ through $P_i^{m-1}$ from the step of reprojecting, and the highest layer producing the calculated projection data set $P_i$; and the step of splitting is organized in a tree-type manner as a plurality of layers and comprises, for each layer, splitting one or more correction projection data strips from the next higher layer to present a greater number of correction projection data strips to the next lower layer, the highest layer splitting the correction data set $E_i$, and the lowest layer producing the correction projection data strips $E_i^0$ through $E_i^{m-1}$.

13. A method in accordance with claim 11, which comprises employing a plurality m of backproject/reproject processors corresponding to the voxel subcubes to perform the steps of reprojecting and backprojecting.

14. A method in accordance with claim 12, which comprises employing a plurality of split/merge processors connected in a tree structure to perform the steps of merging and splitting.

15. A method in accordance with claim 11, which further comprises, during each iteration, for each of the discrete source positions $\theta_i$;

in conjunction with the step of reprojecting each voxel subcube $V^0$ through $V^{m-1}$, calculating data values for a corresponding 2D normalizing factor data strip from a group of 2normalizing factor strips $N_i^0$ through $N_i^{m-1}$ of a 2D normalizing factor data set $N_i$ including a plurality of pixels, the 2D normalizing factor strips $N_i^0$ through $N_i^{m-1}$ overlapping in part;

merging the normalizing factor data strips $N_i^0$ through $N_i^{m-1}$ to calculate element values of the 2D normalizing factor data set $N_i$; and during the step of calculating the 2D correction data set $E_i$, employing each corresponding element of the normalizing factor data set $N_i$.

16. A method in accordance with claim 11, wherein the step of reprojecting is voxel drivel and comprises, for each voxel subcube of the plurality of voxel subcubes $V^0$ through $V^{m-1}$:

initializing the corresponding calculated projection data strip from the group of projection data strips $P_i^0$ through $P_i^{m-1}$; and for each of the selected voxels of the 3D voxel data set V included in the particular voxel subcube, adding to the value of each pixel of the corresponding calculated projection data strip from the group of calculated projection data strips $P_i^0$ through $P_i^{m-1}$ influenced by the selected voxel and voxel value multiplied by a weighting factor h(p,v) determined for the voxel and pixel positions based on geometry such that pixel values are cumulated in the corresponding artificial projection data strip.

17. A method in accordance with claim 15, wherein the step of reprojecting is voxel driven and comprises, for each voxel subcube of the plurality of voxel subcubes $V^0$ through $V^{m-1}$:

initializing the corresponding calculated projection data strip from the group of projection data strips $P_i^0$ through $P_i^{m-1}$;

initializing the corresponding normalizing factor data strip from the group of normalizing factor data strips $N_i^0$ through $N_i^{m-1}$; and for each of the selected voxels of the 3D voxel data set V(v) included in the particular voxel subcube, adding to the value of each pixel of the corresponding calculated projection data strip from the group of calculated projection data strips $P_i^0$ through $P_i^{m-1}$ influenced by the selected voxel and voxel value multiplied by a weighting factor h(p,v) determined for the voxel and pixel positions based on geometry such that pixel values are cumulated in the corresponding artificial projection data strip, and adding to the value of each element of the corresponding normalizing factor data strip from the group of normalizing factor data strips $N_i^0$ through $N_i^{m-1}$ the square of the weighting factor h(p,v) determined for the voxel and pixel positions based on geometry such that element values are cumulated in the corresponding normalizing factor data strip.

18. A method in accordance with claim 16, wherein the step of backprojecting is voxel driven and comprises, for each voxel subcube of the plurality of voxel subcubes $V^0$ through $V^{m-1}$, for each of the selected voxels of the 3D voxel data set V included in the particular voxel subcube, adding to the voxel value the value of each element of the corresponding 2D correction projection data strip of the group of correction projection data strips $E_i^0$ through $E_i^{m-1}$ in a pixel position influenced by the selected voxel multiplied by the weighting factor h(p,v) determined for the voxel and pixel positions based on geometry such that corrected voxel values are cumulated.

19. Parallel processing apparatus implementing the Algebra Reconstruction Technique (ART) for iteratively reconstructing from cone beam projection data a 3D voxel data set V representing an image of an object, the cone beam projection data acquired by employing a cone beam x-ray source and a two-dimensional array detector to scan the object along a source scanning trajectory to obtain, at each of a plurality of discrete source positions $\theta_i$ on the source scanning trajectory, a 2D measured cone beam pixel data set $P_i$, said apparatus comprising:

a data memory for storing the voxel data set V organized as a plurality m of independent voxel subcubes $V^0$ through $V^{m-1}$, each voxel subcube including a plurality of voxels;

processing elements for initializing the voxel data set V and performing successive iterations to correct the values of at least selected voxels of the 3D voxel data set based on the measured cone beam data sets $P_i$, during each iteration correcting the values of at least the selected voxels for each of the discrete source positions $\theta_i$ on the source scanning trajectory, said processing elements including in a level 0 a plurality m of backproject/reprojectors corresponding to the voxel subcubes, and in a level 1 at least one split/merge processor, said backproject/reproject processors operable to reproject each voxel subcube $V^0$ through $V^{m-1}$ to calculate pixel values for a corresponding 2D calculated projection data subset from a group of calculated projection data subsets $P_i^0$ through $P_i^{m-1}$ of a 2D calculated projection data set $P_i$, the projection data subsets $P_i^0$ through $P_i^{m-1}$ overlapping in part, said at least one split/merge processor operable to merge the calculated projection data subsets $P_i^0$ through $P_i^{m-1}$ to calculate pixel values of the 2D calculated projection data set $P_i$, adding pixel values in any overlapping regions of the calculated projection data subsets $P_i^0$ through $P_i^{m-1}$, said processing elements including means for calculating a 2D correction projection data set $E_i$ by determining the normalized difference between the value of each pixel of the measured projection data set $P_i$ the value of the corresponding pixel of the calculated projection data set $P_i$, said split/merge processor operable to split the 2D correction projection data set $E_i$ into a plurality of 2D correction projection data subsets $E_i^0$ through $E_i^{m-1}$ corresponding to the voxel subcubes $V^0$ through $V^{m-1}$, the 2D correction projection data subsets $E_i^0$ through $E_i^{m-1}$ overlapping in part, duplicating element values for any overlapping regions of the correction projection data subsets $E_i^0$ through $E_i^{m-1}$, and said backproject/reproject processors operable to backproject each correction projection data subset $E_i^0$ through $E_i^{m-1}$ to correct voxel values in the corresponding voxel subcube of the plurality of voxel subcubes $V^0$ through $V^{m-1}$.

20. Apparatus in accordance with claim 19, which comprises a plurality of split/merge processors organized as a tree-type structure in a plurality of layers;

said split/merge processors operable to merge groups of calculated projection data subsets from the next lower layer to present a lesser number of calculated projection data subsets to the next higher layer, the lowest layer merging groups of the calculated projection data subsets $P_i^0$ through $P_i^{m-1}$ from the backproject/reproject processors, and the highest layer producing the calculated projection data set $P_i$; and said split/merge processors operable to split one or more correction projection data subsets from the next higher layer to present a greater number of correction projection data subsets to the next lower layer, the highest layer splitting the correction data set $E_i$, and the lowest layer producing the correction projection data subsets $E_i^0$ through $E_i^{m-1}$.

21. Apparatus in accordance with claim 20, wherein at least said split/merge processors comprise transputers.

22. Apparatus in accordance with claim 20, wherein said split/merge processors of each layer each include one I/O port connected to the next higher layer and three I/O ports connected to the next lower layer.

* * * * *